(12) United States Patent
Caravaca-Aguirre et al.

(10) Patent No.: US 10,254,534 B2
(45) Date of Patent: Apr. 9, 2019

(54) SINGLE MULTIMODE FIBER ENDOSCOPE

(71) Applicant: The Regents of the University of Colorado, a body corporate, Denver, CO (US)

(72) Inventors: Antonio Miguel Caravaca-Aguirre, Boulder, CO (US); Rafael Piestun, Boulder, CO (US)

(73) Assignee: The Regents of The University of Colorado, a body corporate, Denver, CO (US)

(*) Notice: Subject to any disclaimer, the term of this patent is extended or adjusted under 35 U.S.C. 154(b) by 0 days.

(21) Appl. No.: 15/365,813

(22) Filed: Nov. 30, 2016

(65) Prior Publication Data

US 2017/0153440 A1   Jun. 1, 2017

Related U.S. Application Data

(60) Provisional application No. 62/261,199, filed on Nov. 30, 2015.

(51) Int. Cl.
| | | |
|---|---|---|
| *G02B 23/24* | (2006.01) | |
| *G02B 23/26* | (2006.01) | |
| *G02B 6/02* | (2006.01) | |
| *H04N 5/247* | (2006.01) | |
| *H04N 5/225* | (2006.01) | |
| *G02B 6/028* | (2006.01) | |

(52) U.S. Cl.
CPC ....... *G02B 23/2469* (2013.01); *G02B 6/0288* (2013.01); *G02B 23/2453* (2013.01); *G02B 23/2484* (2013.01); *G02B 23/26* (2013.01); *H04N 5/2256* (2013.01); *H04N 5/247* (2013.01); *H04N 2005/2255* (2013.01)

(58) Field of Classification Search
None
See application file for complete search history.

(56) References Cited

U.S. PATENT DOCUMENTS

| | | | | |
|---|---|---|---|---|
| 7,821,649 | B2 * | 10/2010 | Bendall | G01B 11/2527 |
| | | | | 356/447 |
| 8,323,956 | B2 * | 12/2012 | Reardon | C12Q 1/002 |
| | | | | 435/177 |
| 9,493,805 | B2 * | 11/2016 | Reardon | C12Q 1/002 |
| 2001/0055462 | A1 * | 12/2001 | Seibel | A61B 1/00048 |
| | | | | 385/147 |

(Continued)

*Primary Examiner* — Reza Aghevli
(74) *Attorney, Agent, or Firm* — Maschoff Brennan; Paul G. Johnson

(57) ABSTRACT

An example multimode fiber endoscope may include an elongated body having a proximal end and a distal end; a multimode fiber disposed within the elongated body and extending from the proximal end to the distal end of the elongated body; a light source disposed relative to the proximal end of the elongated body; a light detector disposed relative to the proximal end of the elongated body; and multiple optical elements disposed between the light source and the multimode fiber. One or more of the optical elements are configured to direct light from the light source into the multimode fiber. One or more of the optical elements are configured to direct light from the multimode fiber to the detector. In some embodiments, the multimode fiber may be a single multimode fiber.

20 Claims, 16 Drawing Sheets

(56) References Cited

U.S. PATENT DOCUMENTS

| | | | | |
|---|---|---|---|---|
| 2003/0135205 A1* | 7/2003 | Davenport | ............ | A61B 18/22 606/3 |
| 2008/0194969 A1* | 8/2008 | Werahera | ............ | A61B 5/0059 600/476 |
| 2009/0225320 A1* | 9/2009 | Bendall | ............ | G01B 11/25 356/447 |
| 2010/0022824 A1* | 1/2010 | Cybulski | ............ | A61B 1/00071 600/104 |
| 2010/0149315 A1* | 6/2010 | Qu | ............ | A61B 1/00193 348/46 |
| 2010/0224796 A1* | 9/2010 | Mertz | ............ | G02B 21/0056 250/459.1 |
| 2011/0205552 A1* | 8/2011 | Bendall | ............ | G01B 11/25 356/606 |
| 2011/0237892 A1* | 9/2011 | Tearney | ............ | A61B 5/0062 600/160 |
| 2012/0051084 A1* | 3/2012 | Yalin | ............ | G02B 6/028 362/553 |
| 2014/0071238 A1* | 3/2014 | Mertens | ............ | A61B 1/07 348/45 |
| 2014/0253705 A1* | 9/2014 | Kummailil | ............ | A61B 1/0638 348/68 |
| 2015/0015879 A1* | 1/2015 | Papadopoulos | ............ | G02B 23/26 356/301 |
| 2016/0206373 A1* | 7/2016 | Chen | ............ | A61B 18/1492 |
| 2016/0227991 A1* | 8/2016 | Hayut | ............ | A61B 1/00009 |
| 2016/0356746 A1* | 12/2016 | Piestun | ............ | A61B 5/0095 |
| 2017/0105618 A1* | 4/2017 | Schmoll | ............ | A61B 3/1025 |
| 2018/0143373 A1* | 5/2018 | Cizm R | ............ | G02B 23/26 |

* cited by examiner

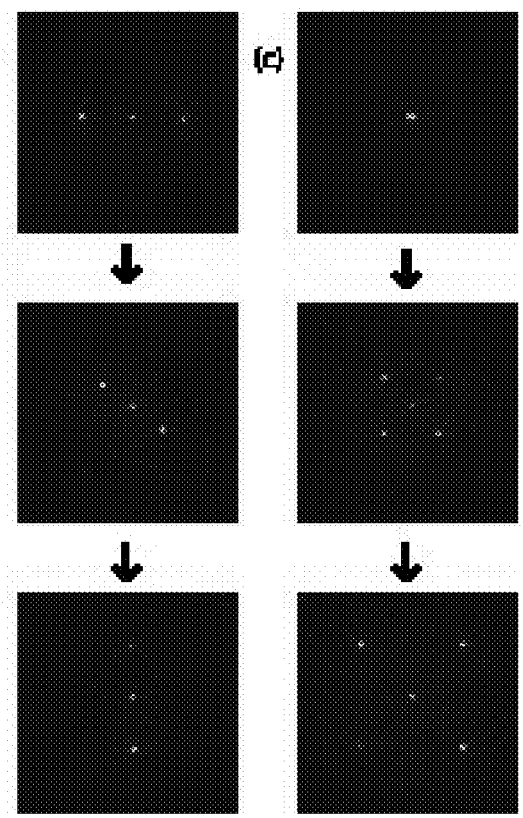
*FIG. 3A*    *FIG. 3B*

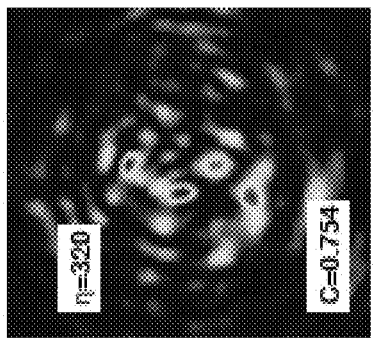
FIG. 6A
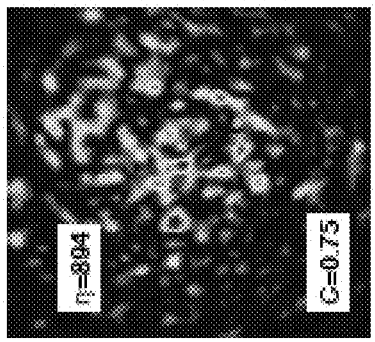
FIG. 6B
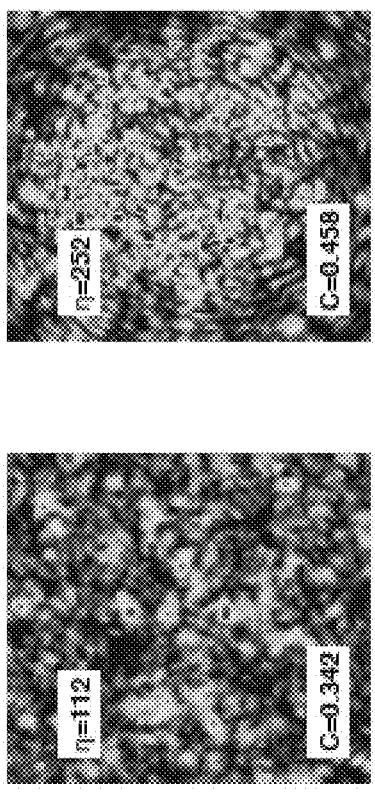
FIG. 6C
FIG. 6D

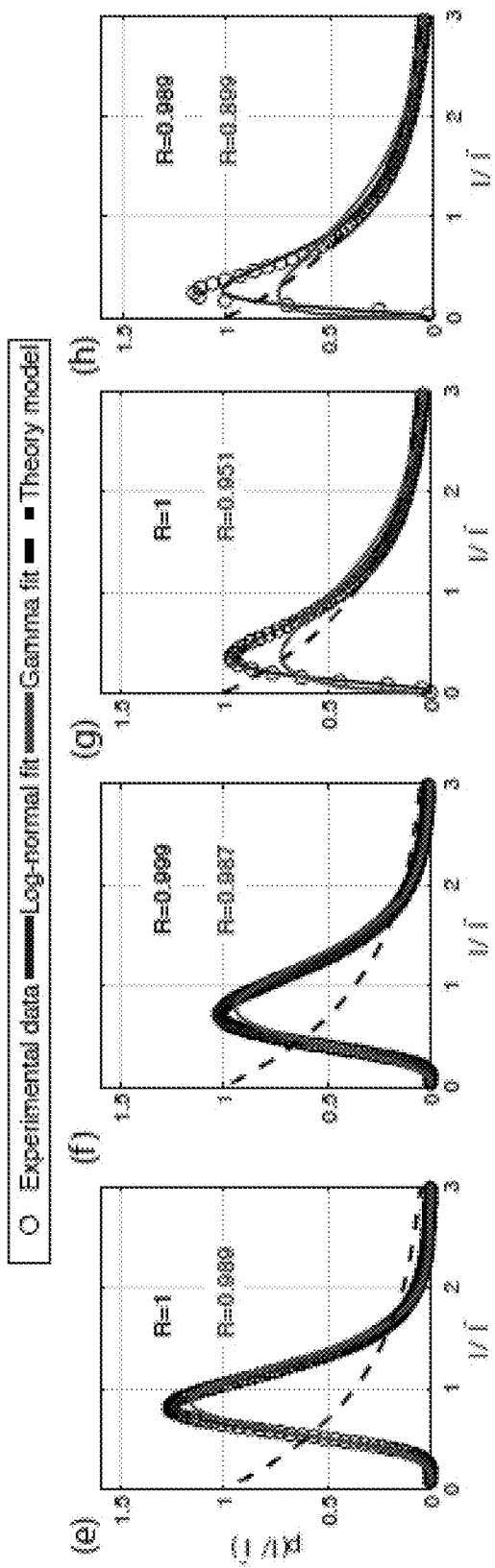

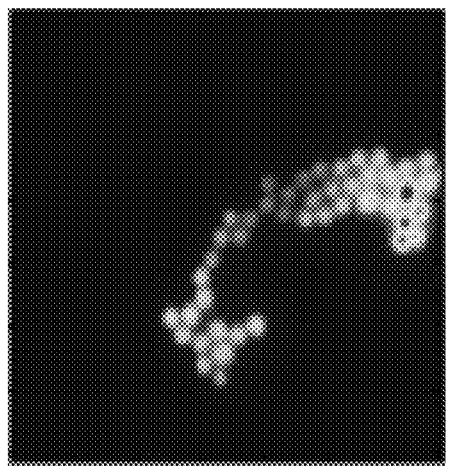 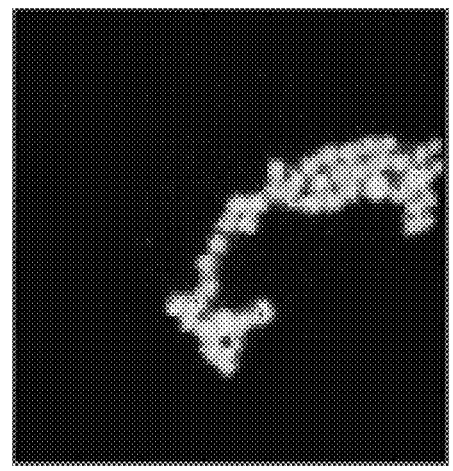 
FIG. 9A  FIG. 9B
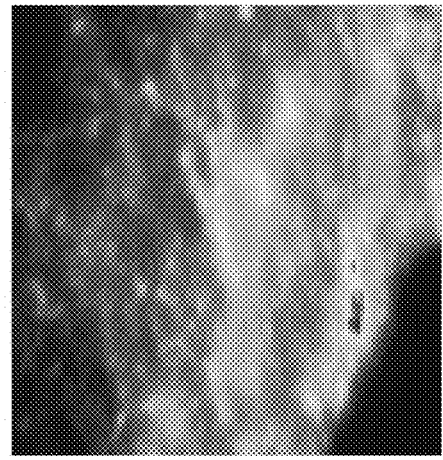 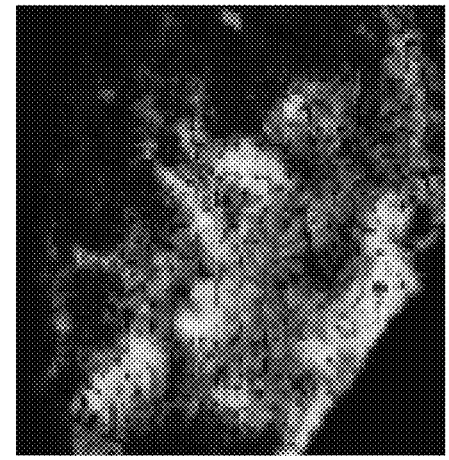
FIG. 9C  FIG. 9D

SINGLE MULTIMODE FIBER ENDOSCOPE

BACKGROUND

Endoscopy imaging typically uses mode fiber bundles, GRIN lenses with motorized parts or hybrid systems of fiber optics and mechanical actuators. The cross section of these devices ranges typically from 0.5 mm up to a few mm, which make them not suitable for a lot of biological applications such as, for example, neuron imaging and optogenetics.

SUMMARY

Some embodiments of the invention include a multimode fiber endoscope. The endoscope may include an elongated body having a proximal end and a distal end; a multimode fiber disposed within the elongated body and extending from the proximal end to the distal end of the elongated body, the multimode fiber; a light source disposed relative to the proximal end of the elongated body; a light detector disposed relative to the proximal end of the elongated body; and a plurality of optical elements disposed between the light source and the multimode fiber, wherein one or more of the plurality of optical elements are configured to direct light from the light source into the multimode fiber, and wherein one or more of the plurality of optical elements are configured to direct light from the multimode fiber to the detector. In some embodiments, the multimode fiber may be a single multimode fiber.

Some embodiments of the invention include an endoscope comprising a multimode fiber having a proximal end and a distal end; a light source disposed relative to the proximal end of the multimode fiber; a spatial light modulator that phase shifts and/or attenuates light from the light source into a first plurality of spatially independent modes prior to the light form the light source being directed through the multimode fiber; a light detector disposed relative to the proximal end of the multimode fiber; and a plurality of optical elements disposed between the light source and the multimode fiber, wherein one or more of the plurality of optical elements are configured to direct light from the light source into the multimode fiber, and wherein one or more of the plurality of optical elements are configured to direct light from the multimode fiber to the detector.

In some embodiments, the spatial light modulator modulates the light to include a plurality of modes that are substantially decoupled when transmitted through the multimode fiber.

In some embodiments, the multimode fiber includes a plurality of modes, wherein the average difference of eigenvalues of the plurality of modes is maximized. In some embodiments, the multimode fiber comprises a single multimode fiber. In some embodiments, the multimode fiber is optimized for robustness to bending while maintaining a well-defined focus.

In some embodiments, the multimode fiber may has an intensity contrast greater than 0.7. In some embodiments, the intensity contrast is calculated using $$C = \sqrt{\frac{\langle I^2 \rangle}{\langle I \rangle^2} - 1} = \frac{\sigma_I}{\bar{I}}.$$

In some embodiments, the multimode fiber is configured to generate light patterns at one end of a multimode fiber while controlling the light wavefronts on the other end.

In some embodiments, the multimode fiber comprises a graded index multimode fiber. In some embodiments, the multimode fiber generates a focus with an averaged peak-to-background ratio ($\eta$) greater than 500.

Some embodiments include a system comprising: a light source; a spatial light modulator that phase shifts light from the light source into a first plurality of spatially independent modes; a beam splitter that splits light from the digital micro-mirror device into a first light beam and a second light beam; a first imager that images the first light beam; a multimode fiber coupler that couples a multimode fiber with the system; a second imager that images light from a distal end of a multimode fiber when coupled with the multimode fiber coupler for each of a second plurality of spatially independent modes; and a processor coupled with the digital micro-mirror device, the first imager and the second imager that creates a transmission matrix from the light received at the first imager and the second imager.

In some embodiments, the first plurality of spatially independent modes is less than the second plurality of independent modes.

In some embodiments, the first plurality of spatially independent modes comprise a plurality of Hadamard elements of a Hadamard orthonormal basis set.

In some embodiments, the first plurality of spatially independent modes are created using a spatial light modulator.

Some embodiments include a method for generating an image. The method comprising: producing light from a light source; phase shifting and/or attenuating the light into a first plurality of spatially independent modes; directing the light into a proximal end of a multimode fiber to produce a spot at a target location; detecting light from a spot of the target location with a light detector through the multimode fiber; and creating an image of at least a portion of the target location from the light detected at each of the points.

In some embodiments, the method further comprises scanning a plurality of spots at the target location; and detecting light from each of the plurality of spots at the target location with a light detector through the multimode fiber.

In some embodiments, the light detected from the target is produced by fluorescent emission, second harmonic generation, and/or a nonlinear process light emission process.

In some embodiments, phase shifting and/or attenuating the light is based on a transmission matrix of the multimode fiber.

In some embodiments, phase shifting and/or attenuating the light produces light through the multimode fiber the multimode with an intensity contrast greater than 0.7.

In some embodiments, phase shifting and/or attenuating the light produces light with a plurality of modes, wherein the average difference of eigenvalues of the plurality of modes is maximized.

These illustrative embodiments are mentioned not to limit or define the disclosure, but to provide examples to aid understanding thereof. Additional embodiments are discussed in the Detailed Description, and further description is provided there. Advantages offered by one or more of the various embodiments may be further understood by examining this specification or by practicing one or more embodiments presented.

BRIEF DESCRIPTION OF THE FIGURES

These and other features, aspects, and advantages of the present disclosure are better understood when the following Disclosure is read with reference to the accompanying drawings.

FIGS. 3A and 3B show two examples of multiple focus created at the distal tip of a multimode fiber according to some embodiments

FIG. 6A-6D are graphs of the probability density function of the intensity according to some embodiments.

FIGS. 7A-7D are graphs illustrate the experimental probability density function according to some embodiments.

FIGS. 9A-9D are images of 4 µm fluorescence beads and a brain monkey slice labeled with Cy3 images with a fluorescence microscope and reconstructed images with multimode fiber scanning endoscope according to some embodiments.

DETAILED DESCRIPTION

Some embodiments of the invention include a multimode fiber endoscope that may, for example, include a single multimode fiber. Some embodiments also include multimode fiber calibration and/or optimization techniques.

Multimode fibers have the advantage of a small cross section down to tens of microns and the ability to bend into small angles; on the other hand, the excitation of multiple transverse modes with different propagation velocities produce an speckle field, product of the interference among all of the propagating modes, dismissing the multimode fibers as imaging device by itself.

Figure 1:
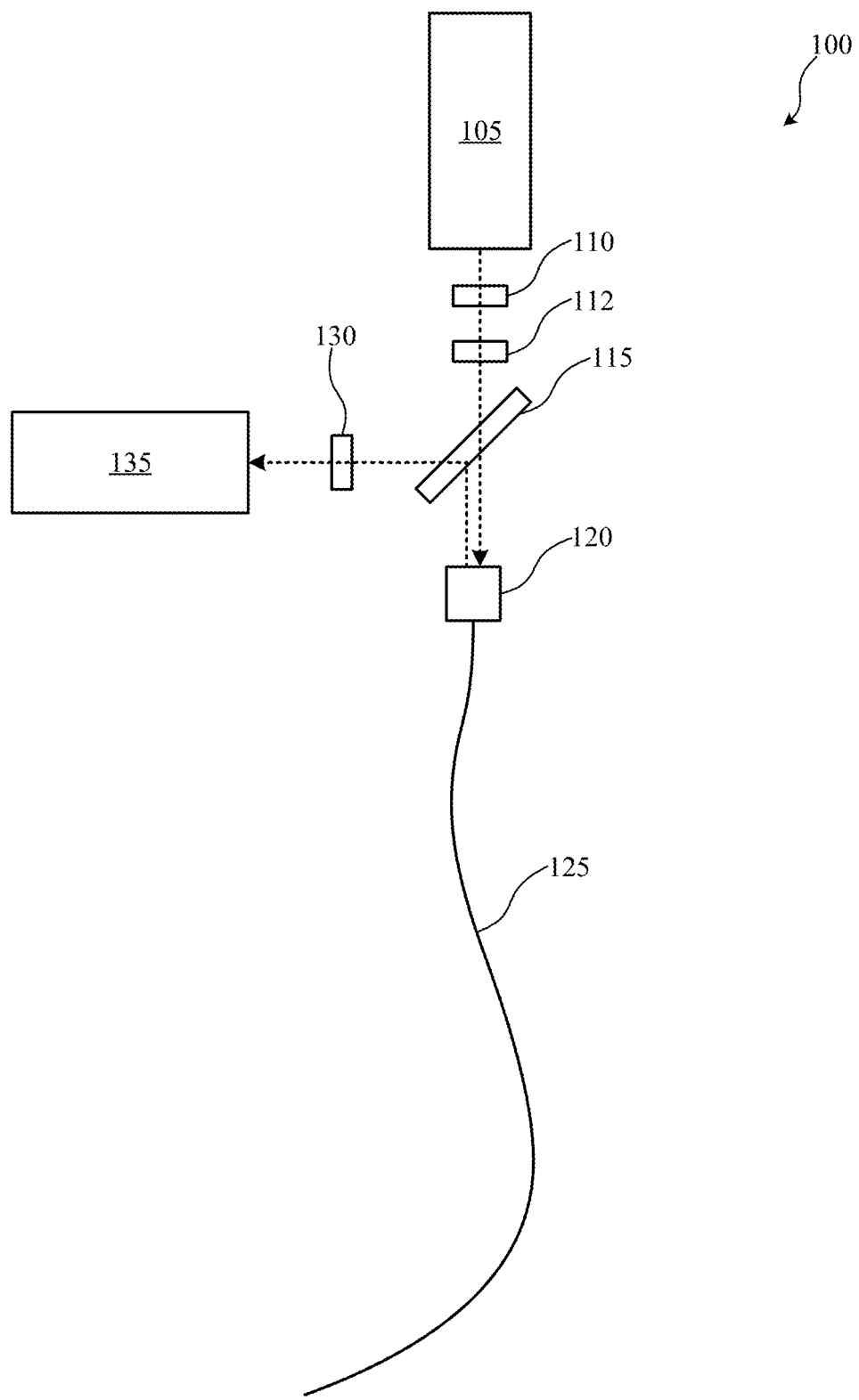
FIG. 1 is a block diagram of an MMF endoscope according to some embodiments.

FIG. 1 is a block diagram of an MMF endoscope 100 according to some embodiments. In some embodiments, the MMF endoscope 100 includes a light source 105, transmission optics 110, a spatial light modulator 112, a light splitter 115, an MMF coupler 120, a multimode fiber 125, receiver optics 130, and/or a detector 135. The MMF endoscope 100 may include any number of other optical elements. In some embodiments, the MMF endoscope 100 may also include a processor coupled with either the light source 105, the detector 135, and/or the spatial light modulator 112.

In some embodiments, light source 105 may include a laser, a laser diode, a diode, etc. In some embodiments, the light source 105 may produce light of any wavelength such as, for example, light within the visible range (e.g., between about 390 nm to 700 nm). In some embodiments, the light source 105 may produce collimated light.

In some embodiments, the transmission optics 110 and/or the receiver optics 130 may include one or more lenses, collimators, mirrors, etc. In some embodiments, the transmission optics 110 may direct light from the light source 105 to the beam splitter 115 and/or from the beam splitter 115 to the multimode fiber 125. In some embodiments, the receiver optics 130 may direct light from the multimode fiber 125 to the beam splitter 115 and/or from the beam splitter 115 to the detector 135.

In some embodiments, the light from the light source 105 may be modulated by a spatial light modulator 112. For example, the spatial light modulator 112 may produce phase shifts in the light from the light source into a first plurality of spatially independent modes prior to light form the light source being directed through the multimode fiber 125.

In some embodiments, the spatial light modulator 112 may include a phase mask and the light is modulated based on the phase mask. In some embodiments, the spatial light modulator 112 may be programmable. For example, the spatial light modulator 112 may be programmed with a phase mask based on a calibrated transmission matrix of the multimode fiber 125 such as, for example, based on embodiments described in this document.

In some embodiments, the spatial light modulator 112 may include any number of optical elements such as, for example, one or more diffractive optical elements, gratings, Dammann gratings, diffusers, phase masks, holograms, amplitude masks, spatial light modulators, and/or prism arrays, etc. In some embodiments, the spatial light modulator 112 may be implemented by a reflective element such as, for example, a deformable mirror, a reflective spatial light modulator, etc. In some embodiments, the spatial light modulator 112 may include a Deformable Mirror Device (DMD). In some embodiments, the spatial light modulator 112 may include a spatial light modulator made of liquid crystals, deformable mirrors, segmented mirrors, acousto-optic deflectors, etc. In some embodiments, the spatial light modulator 112 may be implemented by a transmissive element.

In some embodiments, the transmission optics 110 may be disposed on one or both sides of the spatial light modulator 112.

In some embodiments, the beam splitter 115 may direct light from the light source 105 toward the multimode fiber 125 while also directing light from the multimode fiber 125 toward the receiver 135. Any type of beam splitter may be used. For example, the beam splitter 115 may include a dichroic mirror.

In some embodiments, the MMF coupler 120 may couple light from the beam splitter and/or the light source onto the surface of the multimode fiber 125. In some embodiments, the MMF coupler 120 may include an objective lens. In some embodiments, the MMF coupler may focus light on to the multimode fiber 125 and/or direct light from the multimode fiber 125 toward the beam splitter 115 and/or the detector 135.

In some embodiments, the multimode fiber 125 may include a single multimode fiber. The multimode fiber 125 may have any cladding diameter such as, for example, 30-800 μm. The multimode fiber 125 may have any core diameter such as, for example, 10-500 μm. In some embodiments, the multimode fiber 125 may comprise a graded-index multimode fiber, a step index multimode fiber, an FDDI multimode fiber, an OM1 multimode fiber, an OM2 multimode fiber, an OM3 multimode fiber, an OM4 multimode fiber, a photonic crystal fiber, a photonic bandgap fiber, a micro-structured fiber, a multi-core fiber, etc. In some embodiments, the multimode fiber 125 may be made from glass, soft glass, polymer, etc. In some embodiments, the multimode fiber 125 may have any number of modes such as, for example, more than 100,000, 500,000, 1,000,000 modes.

In some embodiments, the multimode fiber 125 may have an associated transmission matrix that may be determined using any of various embodiments described in this document.

In some embodiments, the multimode fiber 125 may be optimized to increase contrast of its speckle pattern. In some embodiments, the multimode fiber 125 may have an intensity contrast at or near the theoretical value of one. In some embodiments, the multimode fiber 125 may have an intensity contrast greater than 0.6, 0.7, 0.8, or 0.9. In some embodiments, the intensity contrast may be calculated using:

$$C = \sqrt{\frac{\langle I^2 \rangle}{\langle I \rangle^2} - 1} = \frac{\sigma_I}{\bar{I}}$$

where < . . . > indicates an ensemble average and $\sigma_I$ denotes the variance of the intensity.

In some embodiments, the endoscope 100 may have an averaged peak-to-background ratio (η) greater than 300, 400, 500, 600, 700, etc.

In some embodiments, the multimode fiber 125 may include a plurality of modes that are substantially decoupled.

In some embodiments, the multimode fiber 125 has a transmission matrix with an eigenvalue distribution. In some embodiments, the difference of eigenvalues (e.g., the average difference) of the transmission matrix may be maximized.

In some embodiments, the multimode fiber 125 may be optimized for robustness to bending while maintaining a well-defined focus. For example, the multimode fiber 125 may be bent upwards of 1°, 2°, 3°, 4°, 5°, etc. while maintaining a well-defined focus. For example, the multimode fiber may maintain enhancements of between 50 and 100 while being bent upwards of 1°, 2°, 3°, 4°, 5°, etc.

In some embodiments, the multimode fiber 125 may generate light patterns at one end of a multimode fiber while controlling the light wavefronts on the other end.

In some embodiments, the detector 135 may include any type of optical detector such as, for example, a CMOS camera, a CCD camera, photodiodes, etc. In some embodiments, the detector 135 may be coupled with a display that may provide an image captured via the multimode fiber.

Figure 16:
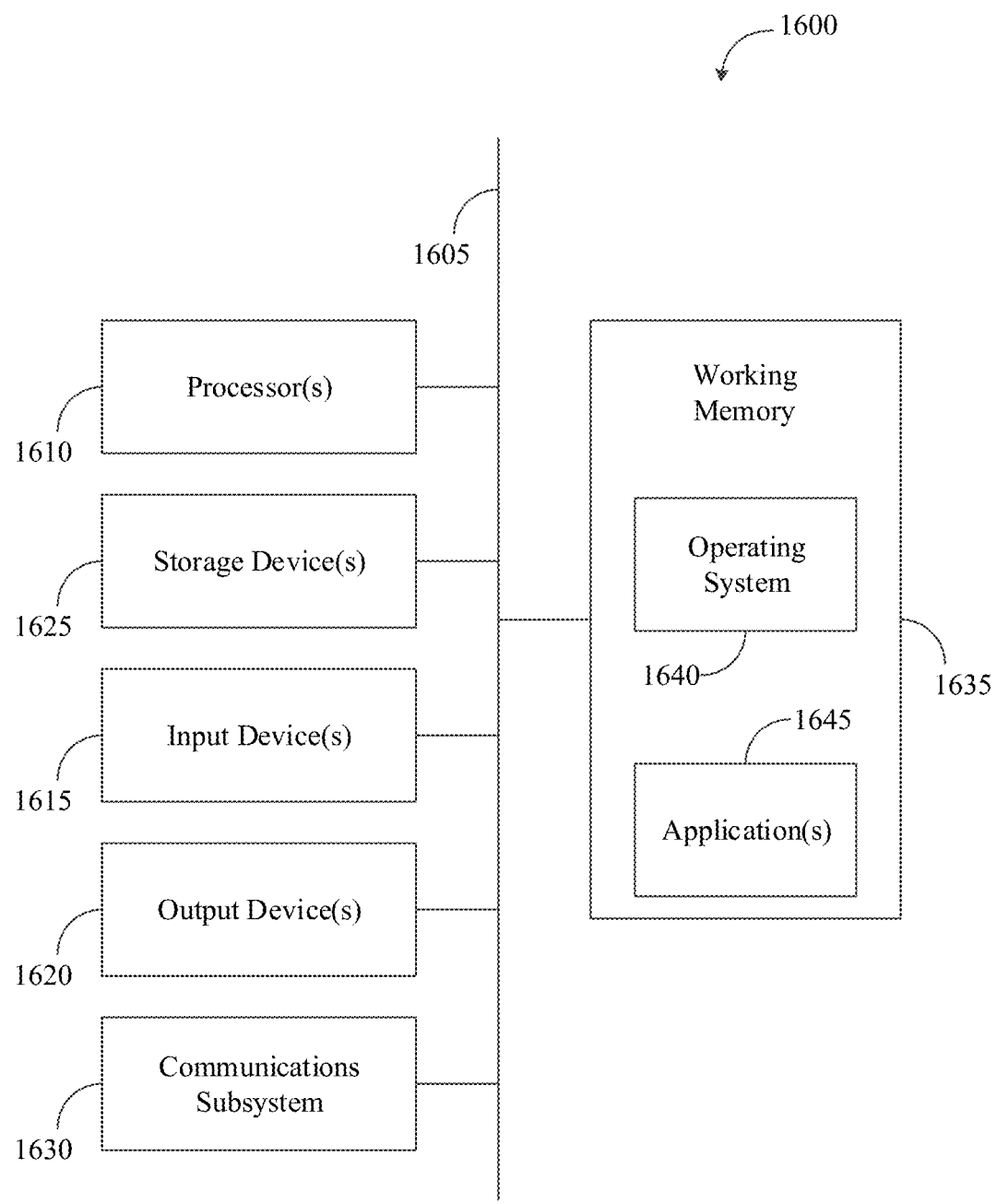
FIG. 16 shows an illustrative computational system for performing functionality to facilitate implementation of embodiments described herein.

In some embodiments, the processor may include any or all the components of the computational system 1600 described in FIG. 16. In some embodiments, the detector 135 may be communicatively coupled with the processor and/or may receive images recorded by the detector 135. The processor may include data describing the transmission matrix of the endoscope 100 and/or the multimode fiber 125. The transmission matrix may be determined, for example, using various embodiments described in this document.

In some embodiments, the processor may control the function of the spatial light modulator 112 and/or the light source 105 to produce a spot through the multimode fiber 125 that is optimized in accordance with various embodiments described in this document that can produce a low speckle image when image by the detector 135 through the multimode fiber 125. For example, the processor may control the function of the spatial light modulator 112 to phase shift and/or attenuate the light from the light source 105 into a first plurality of spatially independent modes prior to the light form the light source being directed through the multimode fiber.

Figure 2:
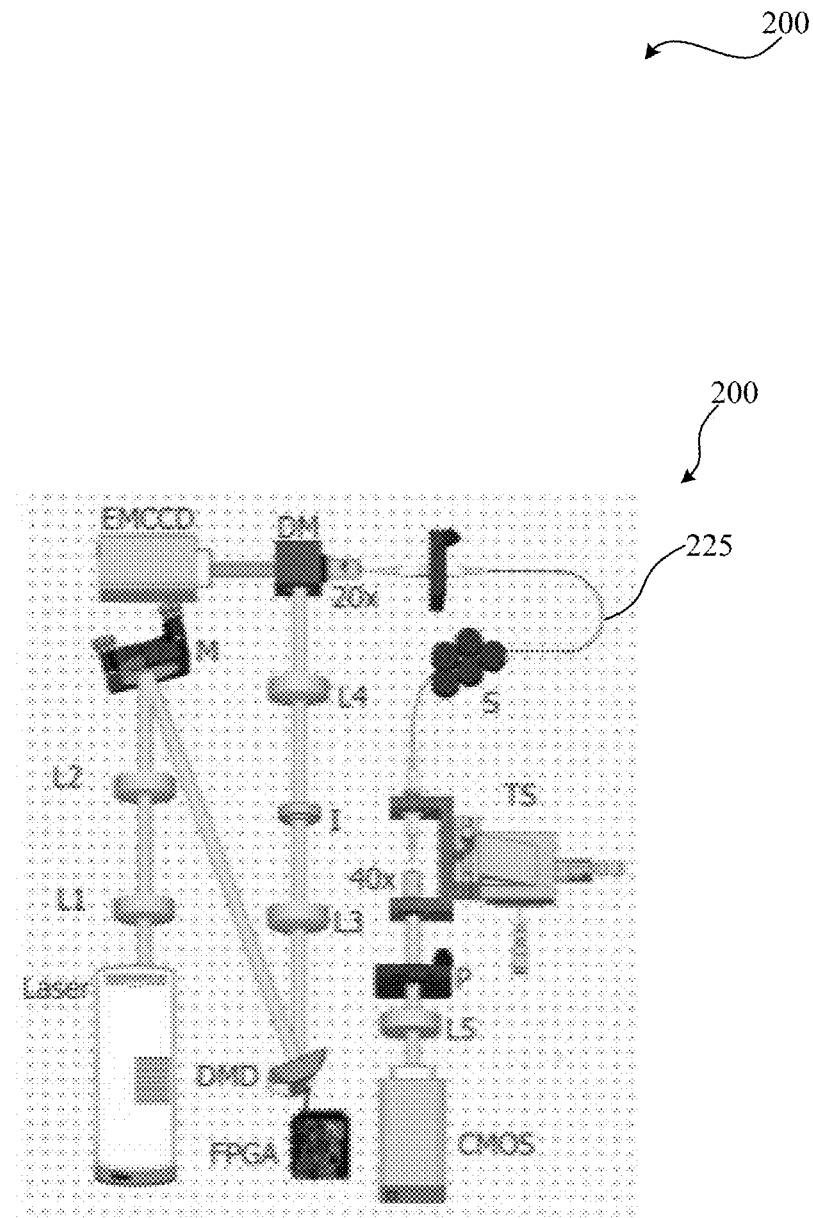
FIG. 2 illustrates a multimode fiber system 200 according to some embodiments.

FIG. 2 illustrates a multimode fiber calibration system 200 according to some embodiments. This calibration system, for example, can be used to measure the statistics of the multimode fiber 225, generate a transmission matrix for the multimode fiber 225, and/or perform fluorescence imaging using the multimode fiber 225. A laser light source is show that can produce a laser beam that beam illuminates L1, L2, L3, L4 and L5: lenses; I: Iris; S: Scrambler; TS: Translation stage; P: Polarizer; and/or BS: Beam splitter.

A spatial light modulator such as, for example, a digital micro-mirror device DMD (e.g., TI-DLP Discovery 4100) may be used to control the phase of the input wavefront using off-axis holography. A custom driver may, for example, allow for high-speed feedback operation. The modulated laser beam may be coupled into the multimode fiber 225 using a microscope objective. The distal tip of the multimode fiber 225 may be positioned within a 2D translation stage and/or may be imaged into a CMOS camera. The system may, for example, allow for control up to 4096 spatially independent input modes to measure the transmission matrix of the multimode fiber 225 using a Hadamard orthonormal basis set. The field of the light exiting the distal tip of the fiber may be recorded for each Hadamard element projected in the DMD using phase shifting interferometry. With knowledge of the measured transmission matrix it is possible to create almost arbitrary intensity distributions at the distal tip of the multimode fiber 225.

FIGS. 3A and 3B show two examples of multiple focus created at the distal tip of a multimode fiber according to some embodiments. These figures show different dynamic patterns created at the distal tip consisting of three and five focus spots. In FIG. 3A three spots rotate clockwise. In FIG. 3B five spots expand outwardly from the center of the fiber.

In some embodiments, the multimode fiber system 200 can be used for fluorescence imaging. In fluorescence imaging a focus spot can be scanned across a sample, which may define the pixel location in the final image. The distal tip of the multimode fiber 225 may collect fluorescence emitted photons from the sample, which may be directed to detector such as, for example, an EMCCD (e.g., Andor iXon3) at the proximal tip of the multimode fiber 225. A dichroic mirror and/or a fluorescence filter may be used to reject the excitation photons. In some embodiments, the detector may also include an avalanche photodiode or photomultiplier tube. In some embodiments, after the focus scanning is finished, a microscopic fluorescence image may be reconstructed. In some embodiments, the DMD may scan the focus at high speed by control of the FPGA. The theoretical resolution of the multimode fiber system 200 may be limited by the size of the speckle created by the multimode fiber 225, which may be a function of the illumination wavelength and/or the numerical aperture of the fiber.

In some embodiments, it can be important to consider in a MMF endoscope the resilience of the calibration to external perturbations. The part of the endoscope that may be likely to suffer perturbations when inserted into the sample is the distal tip of the multimode fiber.

For example multimode fibers are compared. A 200 µm core diameter step-index multimode fiber (e.g., Thorlabs FT200EMT, 0.39NA), a 100 µm core diameter step-index multimode fiber (e.g., Thorlabs UM22-100, 0.22NA), a 100 µm core diameter graded-index multimode fiber (e.g., Newport F-MLD, 0.29NA), and a 50 µm core diameter graded-index multimode fiber (e.g., Corning ClearCurve). The following table summarizes the V-number, ($V=NAa2\pi/\lambda$, where NA is the numerical aperture, a is the radius and $\lambda$ is the wavelength) and the number of propagating modes of each multimode fiber. All of them except the 50 µm core graded-index multimode fiber have a number of modes larger than the number of input modes of our setup controls. The length of each of the four fibers is about 1.5 m; although any length may be used.

| MMF model | Core diameter (µm) | V-number | # of propagating modes |
| --- | --- | --- | --- |
| Thorlabs FT200EMT | 200 | 460 | 85758 |
| Thorlabs UM22-100 | 100 | 129 | 6744 |
| Newport F-MLD | 100 | 171 | 7331 |
| Corning ClearCurve | 50 | 59 | 871 |

Figure 4A:
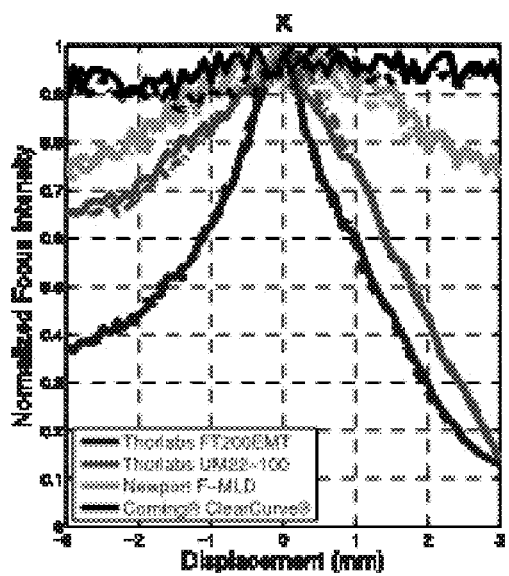
FIGS. 4A and 4B are graphs showing the variation of the normalized intensity value of the focus according to some embodiments.
Figure 4B:
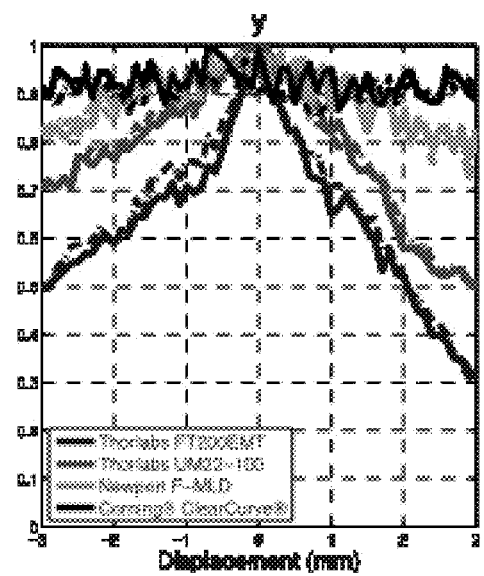

To quantify that robustness, the variation of the focus intensity while the distal tip of the fiber is moved can be analyzed. First, the multimode fiber measuring the transmission matrix can be analyzed. Second, the corresponding hologram that creates a focus at the distal tip of the multimode fiber can be projected onto the DMD. In some embodiments, the distal tip of the multimode fiber can be placed in a translation stage and/or moved in the x and y plane as shown in FIG. 2. A mode scrambler can be disposed 20 cm before the distal tip of the multimode fiber as shown in FIG. 2. The mode scrambler may be used, for example, to produce a more uniform speckle distribution at the output of the multimode fiber. As another example, the mode scrambler can help maintain a fixed position of the fiber. After the calibration, the intensity value of the focus can be recorded at one output mode every 100 µm of displacement. The graphs in FIGS. 4A and 4B shows the variation of the normalized intensity value of the focus according to some embodiments. The solid line indicates the displacement from the origin and the dashed line indicates the displacement towards the origin which show that the original maxima has been recovered. Both graded-index multimode fibers show a more resilient focus intensity to displacements up to 3 mm in both, x and y directions.

The results shown in FIGS. 4A and 4B may be explained using mode-coupling theory. For instance, if the bending produced to the multimode fiber is a small perturbation, the shape of the eigenmodes in the bent region may be the same as in the straight part. The bending of the multimode fiber, for example, may produce one or both of two effects: a change in the propagation constants of the modes in the bent fiber with respect to the straight fiber, and/or coupling between propagating modes. The change in the propagation constants may produce a small change in the output field due to the fact that the perturbation is produced mostly at the end of the fiber, (e.g., mimicking the perturbation when a multimode fiber is introduced in the sample) as shown in FIGS. 4A and 4B as the slow decrease of the peak intensity in both graded index multimode fibers. To evaluate the difference in mode coupling between both types of multimode fiber the power mode-coupling equation can be used:

$$\frac{dP_m}{dz} = -\gamma_m P_m + \sum_{m' \neq m} d_{mm'}(P_{m'} - P_m)$$

This equation may describe the evolution of the power of the eigenmodes, where $P_m$ is the modal power, $\gamma$ is the attenuation coefficient and $d_{mm'}$ is the coupling coefficient between modes with principal mode number m and m'. This equation may assume the attenuation is negligible for the length of the fiber. The selection rules only allow coupling between modes with $\Delta m = \pm 1$. The coupling coefficient can be derived for both cases, graded-index and step-index multimode fiber:

$$d_{GI,m} = \frac{1}{8}(nka)^2 \left[\frac{m}{M}\right] C(\beta_m - \beta_{m'})$$

$$d_{SI,m} = \frac{1}{8}(nka)^2 C(\beta_m - \beta_{m'})$$

where n is the core refractive index, k is the wave number in free space, a is the radius, m is the mode family number, $M^2$ is the total number of modes, and $C(\Delta\beta)$ is the power spectrum of the curvature function, c(z). These equation shows the coupling is stronger in the step index fiber case. In some embodiments, the step-index multimode fiber may exhibit mode couplings that makes the intensity peak to decrease faster.

Figure 5A:
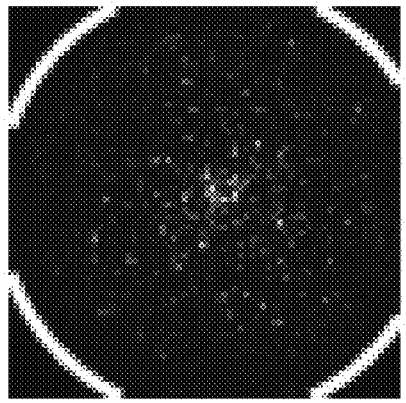
FIGS. 5A-5E illustrate the focus evolution while the multimode fiber is perturbed and released according to some embodiments.
Figure 5B:
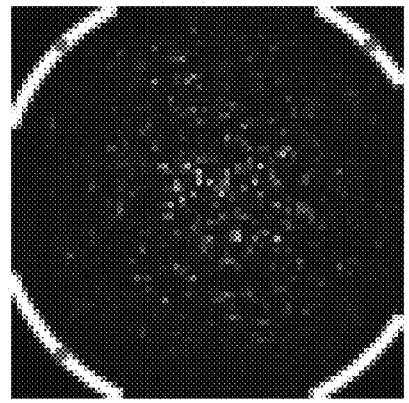
Figure 5C:
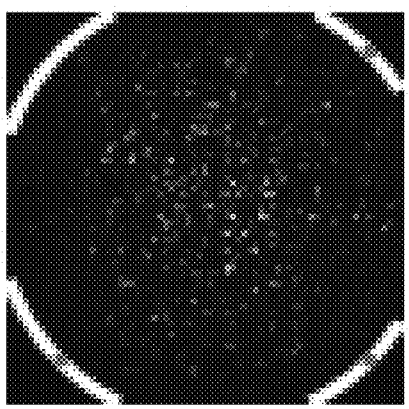
Figure 5D:
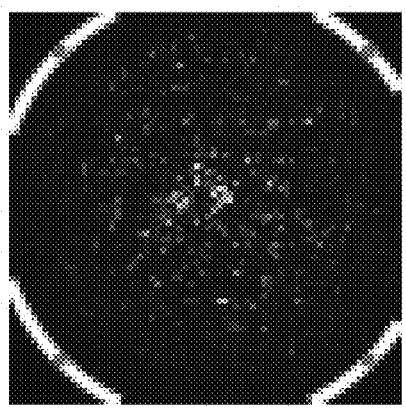
Figure 5E:
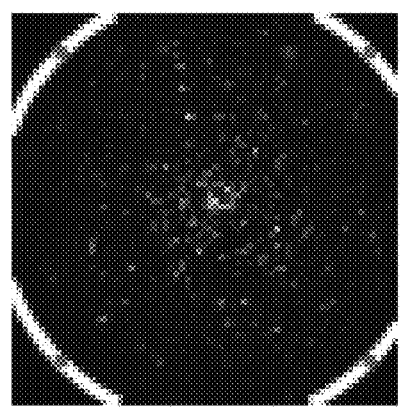

FIGS. 5A-5E illustrate the focus evolution while the multimode fiber is perturbed and released according to some embodiments. The validity of the calibration in a more uncontrolled case when the fiber comes back to its original position after the perturbation is shown in FIGS. 5A-5E. These figures show five snapshots of a recorded movie, corresponding to the intensity at the distal tip of the fiber as it is pressed with a finger and released. In some embodiments, the focus regains its primary enhancement without re-calibration as shown in FIGS. 5A and 5E. In some embodiments these results can be interpreted as encouraging the use of graded-index as a candidate for an endoscope. FIGS. 5A and 5E are graphs of focus evolution while the multimode fiber is perturbed (pressed with a finger) and released. The image may be saturated to appreciate better the focus and the speckle field at the same time. The white curve delimits the border of the multimode fiber.

In some embodiments, the speckle pattern created by each multimode fiber can be examined. A common parameter used to describe the speckle is the intensity contrast, C, defined as $$C = \sqrt{\frac{\langle I^2 \rangle}{\langle I \rangle^2} - 1} = \frac{\sigma_I}{\overline{I}}$$

where ⟨ ... ⟩ indicates an ensemble average and $\sigma_I$ denotes the variance of the intensity. A fully developed speckle created by the interference of a large number of partial waves with phases uniformly distributed over $2\pi$ has a contrast value of 1. A lower value of C indicates deviations from the fully developed speckle regime. Because wavefront shaping combines multiple speckle output modes to create a bright focus, a better contrast will lead to a larger constructive interference between different speckles, while a low contrast will lead to a small intensity enhancement factor.

In some embodiments, the intensity of the light exiting the distal tip of the fiber for each Hadamard element projected in the DMD can be recorded. The polarizer may be disposed between the distal tip of the fiber and the camera to measure only one polarization. The pixel size in each case may be smaller than the speckle grain. For each intensity image a value for C can be calculated. FIGS. 6A-6D show the normalized intensity image of the speckle at the distal tip of different multimode fibers under similar illumination conditions (e.g., during the transmission matrix measurement).

As shown in FIG. 6A-6D show the speckle intensity image of the distal tip of the fiber according to some embodiments. FIG. 6A shows the speckle intensity for a Thorlabs FT200EMT multimode fiber; FIG. 6B shows the speckle intensity for a Thorlabs UM22-100 multimode fiber, FIG. 6C shows the speckle intensity for a Newport F-MLD multimode fiber, and FIG. 6D shows the speckle intensity for a Corning ClearCurve multimode fiber. The bottom insets indicates the speckle contrast, C, for each fiber and the top inset indicates the mean of the enhancement of the focus created at 1000 different output modes In some embodiments, each fiber may produce a speckle pattern that has different contrast and intensity distributions from each other. The mean contrast value for each multimode fiber is shown in the bottom inset of each plot. From those values, we can determine that the multimode fibers shown in FIGS. 6C and 6D, which include the 100 μm and 50 μm graded index multimode fiber, produce a speckle field more similar to a fully developed speckle compared to the other fibers. For instance, with a contrast value closer to the theoretical value of 1. It is interesting to notice that while in modal noise experiments of the prior art, the aim is to reduce the contrast to 0 and destroy the speckle structure to avoid errors, in some embodiments the aim is to increase the contrast to nearly 1.

To explore the implications of the speckle intensity contrast on the performance of each fiber the peak-to-background ratio of a focus that we can create using wavefront shaping can be compared. Using the information of the measured transmission matrix, for example, the optimal pattern at the DMD can be projected creating a focus at the distal tip of the multimode fiber. In some embodiments, one focus at a time at 1000 different output modes can be created using the enhancement of each focus to calculate averaged peak-to-background ratio of the multimode fiber, η. The η value for each fiber is shown in the top inset of each plot in FIGS. 7A-7D. An experimental correlation between the value of intensity contrast, C, and the averaged peak-to-background ratio η can, for example, be found. A speckle contrast closer to 1 corresponds to larger averaged peak-to-background ratio (T)) values and possibly a better quality of the focus. The lower mean enhancement of 50 μm graded-index multimode fiber compared to 100 μm graded-index multimode fiber is due to the lower number of propagating modes. On the other hand, it outperforms the 100 μm step-index multimode fiber due to the difference in the speckle contrast.

Another possible difference between the speckle field created by a scattering medium and a multimode fiber is the intensity statistics that they follow. In some embodiments the probability density function of a multimode fiber can follow a gamma distribution:

$$p(I) = \frac{1}{\Gamma(m)}\left(\frac{I}{\bar{I}}\right)^{m-1}\exp\left(-\frac{I}{\bar{I}}\right)$$

where the factor m is defined as $m = \frac{1}{2}\kappa N_m$, where K is the ratio between the detector size and the core size and $N_m$ the number of transverse modes of the multimode fiber.

In some embodiments, not only is the intensity contrast different among the fibers, but the intensity distribution of the speckle patterns is also different. The statistics of the intensity distribution at the distal tip of the fiber for the entire set of phase masks projected during the transmission matrix measurement (each of them produces a different realization of the speckle pattern at the distal tip of the fiber) can be analyzed. An example plot of the probability density function of the intensity is shown in FIGS. 6A-6D. FIGS. 7A-7D illustrate the experimental probability density function in black circles. The red line is a numerical fit of the experimental data to a gamma distribution. In the examples discussed in this document, both graded-index multimode fibers have a different probability density function than a gamma distribution failing to fit the values at the top of the curve. The experimental data may be fit with a lognormal distribution (blue line) finding a better agreement between them. In some embodiments, the lognormal distribution may be given by:

$$p(I) = \frac{\bar{I}}{I\sigma\sqrt{2\pi}}\exp\left(\frac{-[\log(I/\bar{I})-\mu]^2}{2\sigma^2}\right)$$

where σ and μ are the standard deviation and the mean of the normally distributed log (I/Ī). The inset in FIGS. 7A-7D shows the coefficient of determination, R, of each fitting curve and the experimental data. FIGS. 7A and 7B show that both step index multimode fibers can be described well with both distributions. In some embodiments, the gamma distribution may fail in both graded-index fibers, while the lognormal distribution has an R value close to one. In both graded-index multimode fiber cases, the PDF is more similar to a negative exponential as shown with a dashed black line in FIGS. 7A-7D. This may indicate the scrambling and interference between modes may be more similar to a scattering material.

Figure 8:
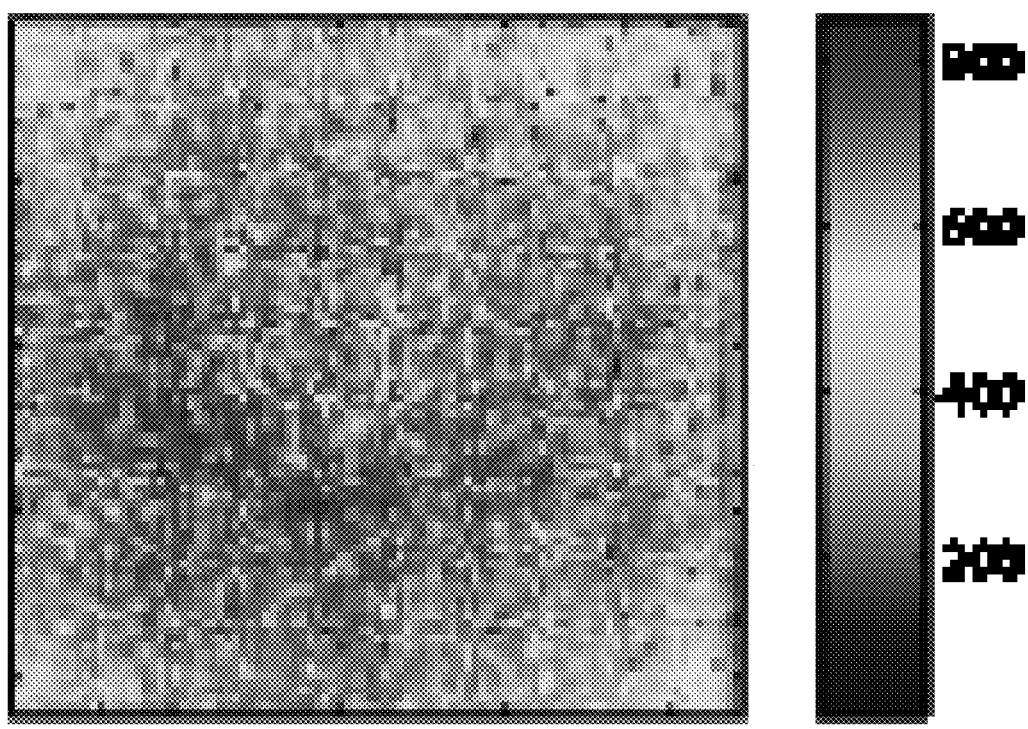
FIG. 8 shows a colormap of the peak-to-background ratio achieved in each focus created at the distal tip using a plurality of input modes.

In some embodiments, different fluorescence samples may be imaged through the multimode fiber. In some embodiments, once the measurement of the transmission matrix is finished and the multimode fiber is calibrated a focus at the distal tip in every output mode at a time is created. FIG. 8 shows a colormap of the peak-to-background ratio achieved in each focus created at the distal tip using a plurality (e.g., 4096) input modes. In some embodiments, the plot may reflect that the intensity of the focus created is consistent and uniform, which may be beneficial in scanning microscope or an endoscope. After the calibration, a fluorescence sample ~100 μm may be placed far from the distal tip. All the input patterns corresponding to the scanning focus may be placed at the distal tip and/or the fluorescence signal that is emitted back through the fiber using an EMCCD may be measured. This approach may convert the multimode fiber in a scanning fluorescence microscope. FIG. 9A shows images of a sample composed of 4 μmm diameter fluorescence beads imaged with a fluorescence microscope. FIG. 9B shows images of a sample composed of 4 μmm diameter fluorescence beads imaged with a multimode endoscope (e.g., the endoscope 100). FIG. 9C shows images of a sample composed of 4 μmm diameter fluorescence beads demonstrating a multimode fiber endoscope that is able to resolve 4 μm beads. The difference in the location of the maxima may be due to the fact that the beads are not in the same plane. FIG. 9C and FIG. 9D show a more interesting and complex sample. A monkey brain slice labeled with Cy3 is imaged using the same technique. Besides imaging only one axial plane, the system could be used to calibrate the fiber in multiple output planes allowing scanning the focus in the axial direction by just modifying the input wavefront previously recorded.

In some embodiments the singular value decomposition of the transmission matrix eigenvalues may be used to select a multimode fiber. In some embodiments, the observed transmission matrix, $K_{obs}$, which may include the transmission matrix of the fiber, K, may be recorded; and/or the contribution from the static reference wavefront, $S_{ref}$, may be recorded, which may, for example, be placed around the Hadamard elements in the DMD and used for the phase shifting interferometric method. To study the singular value decomposition of K we need to remove the contribution of $S_{ref}$ because this matrix introduces correlations. The contribution of $S_{ref}$ may be the same for each input vector. To remove that contribution we may filter the observed transmission matrix dividing it by the variance of each column (input mode). The elements of the filtered matrix, $K_{fil}$, may be given by:

$$k_{mn}^{fil} = \frac{k_{mn}^{obs}}{\sqrt{\langle|k|^2\rangle_{mn}|s_{mn}^2|}} = \frac{k_{mn}}{\sqrt{\langle|k|^2\rangle_{mn}}}\frac{s_{mn}}{|s_{mn}|} = \frac{K}{\sqrt{\langle|k|^2\rangle_{mn}}} \times S$$

where S is a unitary matrix. K, for example, may have the same singular value decomposition as $K_{fil}$.

In some embodiments, the singular values, $\check{\lambda}_i$, may be normalized in order to compare them with the results of random matrix theory. random matrix theory predict the eigenvalue distribution will be described by $$\rho(\check{\lambda}) = \frac{\gamma}{2\pi\check{\lambda}}\sqrt{(\check{\lambda}^2 - \check{\lambda}_{min}^2)(\check{\lambda}_{max}^2 - \check{\lambda}^2)}$$

with $\check{\lambda}_{min} = 1 - \sqrt{1/\gamma}$ and $\check{\lambda}_{max} = 1 + \sqrt{1/\gamma}$ where $\gamma = M/N$ which is the ratio between output modes and input modes.

Figure 10A:
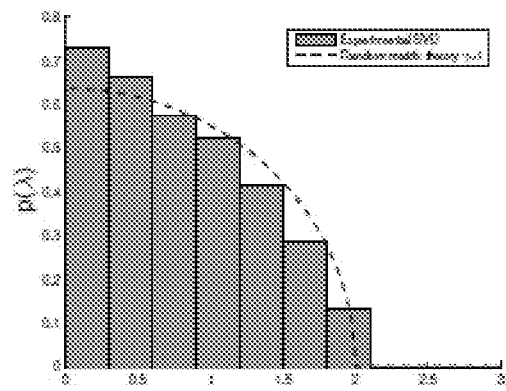
FIGS. 10A-10F show the comparison between the random matrix theory prediction and some experimental results for two scattering samples according to some embodiments.
Figure 10B:
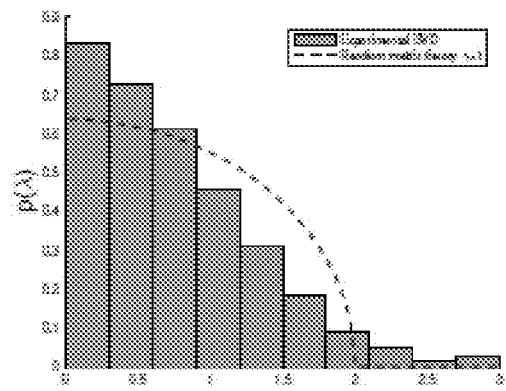
Figure 10C:
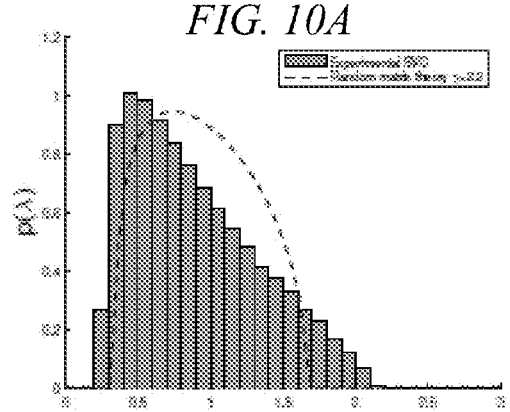
Figure 10D:
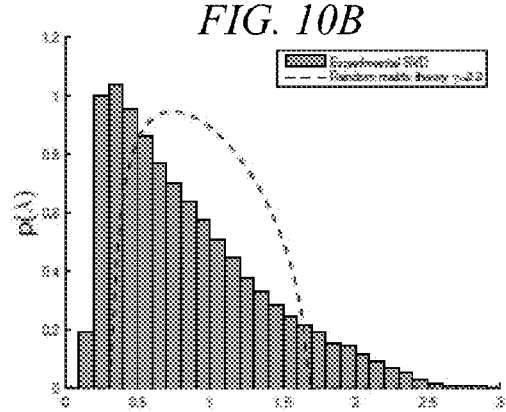
Figure 10E:
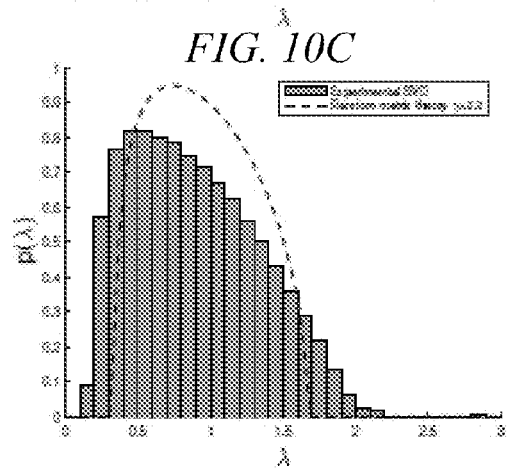
Figure 10F:
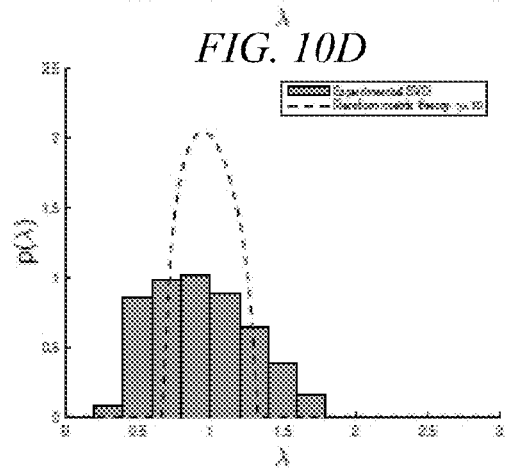

FIGS. 10A and 10B show the comparison between the random matrix theory prediction (dashed line) and some experimental results (histogram) for two scattering samples: an eggshell and a glass diffuser. In this example, the number of input modes for both experiments is 256 and the number of output modes correspond to 1024. Once every two pixels of the output modes are removed to avoid correlations between neighboring pixels reducing the γ value to 1. In the case of the eggshell the normalized eigenvalue distribution follows the quarter circle law. The glass diffuser (FIG. 10A) shows a distribution which slightly deviates from the theoretical curve revealing some extra correlation. This difference may indicate that the glass diffuser may or may not be as strong of a scattering sample as the eggshell, and some speckle field correlations such as the memory effect may still remain when the light goes through it. The singular value decomposition of the transmission matrix of the two step index multimode fibers and the two graded-index multimode fibers is shown in FIGS. 10C 10F. In the four examples, the number of input modes may be set to 4096. The number of output modes may be set at 29,568 except in FIG. 10F (Corning Clearcurve 50 μm core diameter) which is 8100. The full width half maximum of the autocorrelation function, which determines the speckle grain size, corresponds to four pixels in the four cases. Therefore, four of every other pixel are removed to avoid the correlations between neighboring pixels. In some embodiments, the distribution does not match with the random matrix theory prediction, although it follows a similar trend. The existence of some correlation in the speckle field created by the multimode fiber, such as the rotational memory effect, may be responsible for this mismatch. This result suggests that those correlations are hidden in the transmission information. In the Corning Clearcurve 50 μm diameter multimode fiber, due to the large number of modes measured in comparison with the modes available in the multimode fiber, a bimodal distribution may be expected. In some embodiments, missing the left and right maxima corresponding to the close and open channels may be due to the incomplete mode control.

Some embodiments may include a real-time phase mask optimization technique through a multimode fiber using a transmission matrix measurement technique. The algorithm, for example, may be implemented in a processor (e.g., an FPGA), which may control a DMD at full speed, improving one order of magnitude the overall focusing time with respect to our previous system that was applied in scattering materials. Such embodiments may overcome fiber perturbation effects at video frame rates (e.g., rates greater than 15 frames per second).

The optimization technique may be performed using the system shown in FIG. 2. Alternatively or additionally, the optimization technique may be performed using the system shown in FIG. 11, which may include a 532 nm collimated laser beam that illuminates a binary amplitude digital micromirror device (DMD) (e.g., DMD TI-DLP Discovery Kit D4100; 1024×768). Each mirror of the digital micromirror device can be controlled, for example, to two different angular positions, essentially creating a binary amplitude image. To control the phase of the beam, a binary amplitude Lee hologram may encode the desired wavefront with the DMD. A lens, f1, placed one focal length away from the DMD, Fourier transforms the hologram and an iris in the Fourier plane blocks all the diffraction orders except the 1st, which encodes the information of the desired phase distribution. The lens f2 may be used to image the phase mask on the back focal plane of a 10× objective (e.g., NA=0.25) that couples the light into a 365 μm core diameter multimode fiber, 0.22 NA (e.g., BFL22-365-Thorlabs), which can propagate an estimated $1.1\times10^5$ modes.

Figure 11:
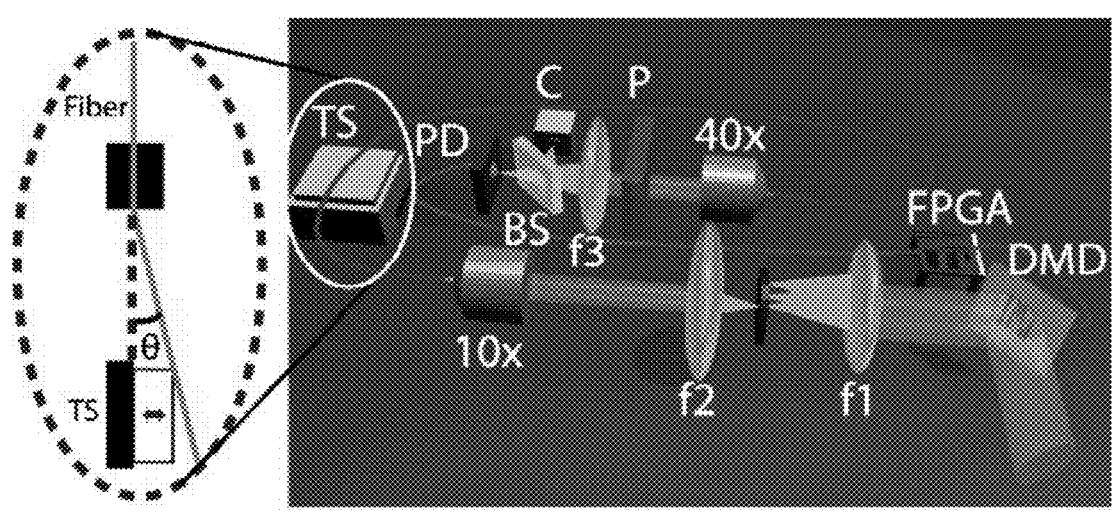
FIG. 11 illustrates a system that may be used for optimization of a multimode fiber according to some embodiments.

At the output of the multimode fiber, the light is received by a 40× objective (e.g., NA=0.65) which images the surface of the fiber onto a 50 μm pinhole placed before a photodetector. The objective magnification and the pinhole size may, for example, be chosen to match the pinhole diameter to the speckle spot size at the image plane. To control and characterize the movement of the multimode fiber, an automated translation stage that bends the fiber by a measurable angle may be used as shown in the inset of FIG. 11.

A beam splitter placed after the tube lens and before the pinhole may be used to create a second image plane on a CMOS camera (e.g., Hamamatsu ORCA Flash 2.8) which may enable high frame rate video recording for data analysis and speckle decorrelation time measurement. The photodetector signal may be digitized by an analog-to-digital converter and/or triggered by processor (e.g., an FPGA that may be placed on the DMD controller board). The intensity values are oversampled and the average value may be used to build the hologram with the optimal phase mask encoded to produce the focus spot.

Figure 12:
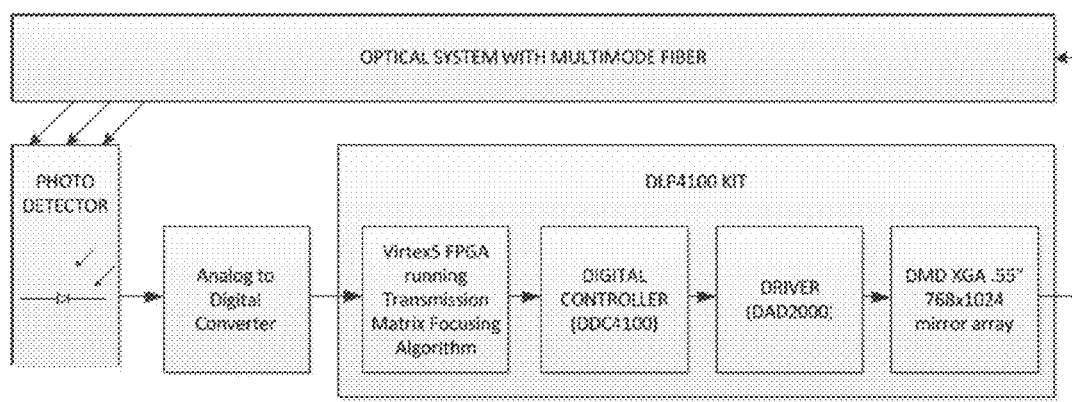
FIG. 12 shows a high-level block diagram of the hardware implementation of the transmission matrix focusing system according to some embodiments.

In some embodiments, a hardware implementation may be useful to reduce latency and computation times. A phase shifting method based on three measurements per input mode for transmission matrix determination may be implemented directly using a processor (e.g., a Virtex5 custom FPGA). A separate analog-to-digital converter (ADC), with a buffered analog input, digitizes the signal and provides the input to the processor. A controller (e.g., DDC4100 and/or DAD2000 or the processor) may control the DMD. The controller or the processor may also be responsible for accurate triggering of the analog signal conversion and/or storage of the digitized output. FIG. 12 shows a high-level block diagram of the hardware implementation of the transmission matrix focusing system according to some embodiments. This configuration is independent of an external computation source and therefore able to toggle the DMD at the maximum frame rate. In some embodiments, the system may enable measurement of the amplitude and phase corresponding to more than 256 different input modes (with three different reference phases per input mode), for example, in 33.8 ms, corresponding to an update frequency of 22.7 KHz. Processing this information to construct the optimal phase mask, then sending to and projecting on the DMD may add some addition time (e.g., 3 ms). The optimized, focusing phase mask projection time can be varied based on various conditions. In some embodiments, focusing time maybe matched with the measurement time. For example, a measurement time of 37 ms, which provides a 50% duty cycle and allows for repetitive focusing at a constant rate of 13 Hz.

To quantify the performance of the system, for example, the fiber may be bent with different speeds and accelerations to create a dynamic environment. Bending the fiber alters the mode coupling within the fiber; which may be manifested by a speckle pattern change at the fiber output. The speckle pattern change may be quantified by measuring the 2D correlation between the speckle pattern associated with a bent fiber and a straight fiber. By analyzing the correlation between captured speckle image frames from the CMOS using a static input illumination, the average decorrelation time associated with each setting of the stage may be obtained.

Figure 13A:
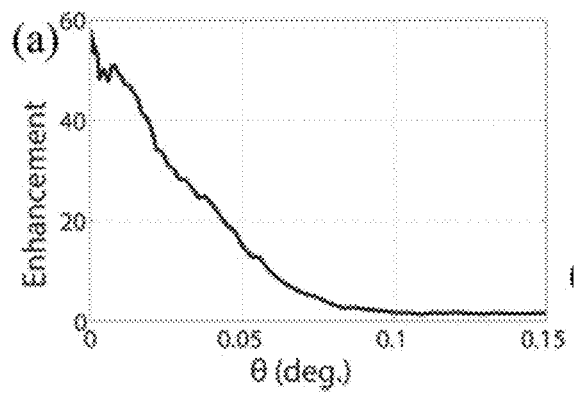
FIG. 13A shows how displacing the fiber less than 0.1 mm can correspond to bending the fiber just 0.09°.
Figure 13B:
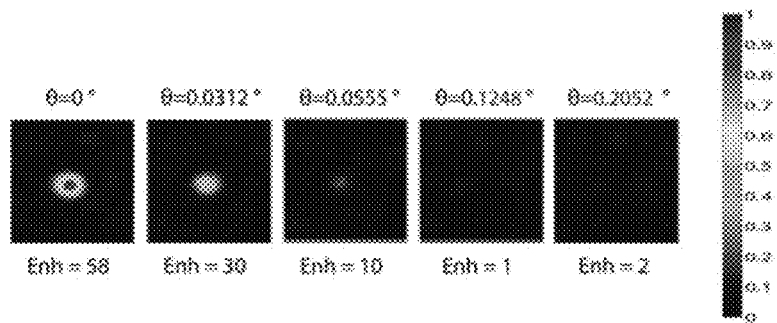
FIG. 13B and FIG. 13C show the output field intensity of the fiber taken by the camera at different positions of the translation stage according to some embodiments.
Figure 13C:
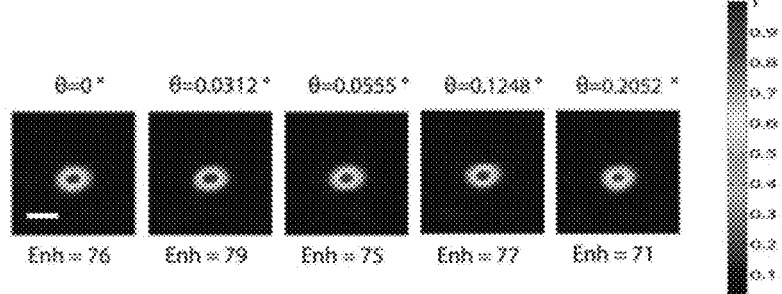

To illustrate the sensitivity of the fiber to spatial changes, in some embodiments, the focus degradation may be measured as the fiber is bent without adaptive correction. FIG. 13A shows how displacing the fiber less than 0.1 mm can correspond to bending the fiber just 0.09°, the focus may disappear. This illustrates the high sensitivity of a multimode fiber to spatial displacements due to mode coupling. To demonstrate the performance of the system, the degradation of the focus spot can be compared for two cases: a) with a static phase mask, and b) with adaptive wavefront correction. FIG. 13B and FIG. 13C show the output field intensity of the fiber taken by the camera at different positions of the translation stage according to some embodiments. FIG. 13B illustrates how bending the fiber quickly degrades the created focus when the phase mask is not re-optimized. In FIG. 13C, the image is shown at the output of the fiber with the adaptive system on. The stage moves with an initial acceleration of 2 mm/s$^2$ until reaching a constant velocity of 1 mm/s, corresponding to an average speckle decorrelation time of 150 ms. Despite the fast rate of change, the focus enhancement remains high and stable. Note that the enhancements at $\theta=0°$ in FIGS. 13B and 14C do not match because the enhancement achieved is highly sensitive to the initial conditions.

Figure 14:
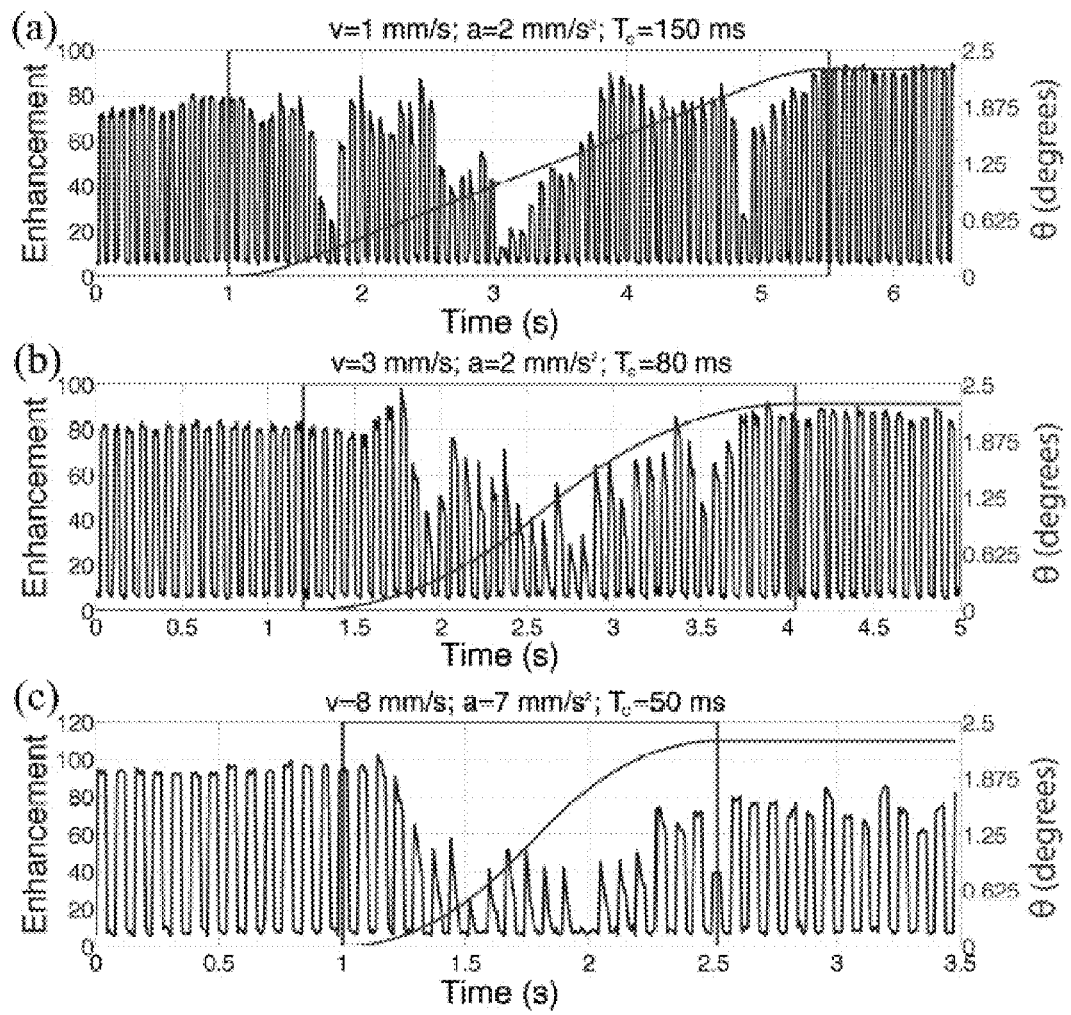
FIG. 14 shows graphs of the singular value decomposition of a transmission matrix for six different elements according to some embodiments according to some embodiments.

To test the efficiency of the system, the dynamics of the focus enhancement can be tracked as a function of time as the fiber bends as shown in the blue line of FIG. 14. The zone delimited by the red line corresponds to the interval when the stage is moving. The bending angle of the fiber as a function of time is represented in green. The enhancement is constant while the stage is not moving. Once the stage starts moving, the enhancements achieved with the bending fiber may be smaller and more variable than with a static fiber, which may be due to the dynamics of the transmission matrix; the result of performing measurements while the system is changing.

It is worth noting that in some embodiments even for an average decorrelation time of 50 ms, close to the system cycle time (37 ms), the enhancement obtained does not fall too low, with values around 40. In this case, some of the modes measured have changed after 37 ms, which is the period from the first measurement to the projection of the optimal phase mask, explaining the lower enhancement. Furthermore, a higher number of input modes could be used to increase the enhancement as a tradeoff to speed. While small angle bends are described in accordance with some embodiments, larger angle bends lead to similar enhancement.

Some embodiments include real-time focusing through a dynamically bending multimode fiber that may, for example, be used in an endoscope. In some embodiments, the multimode fiber may have more than 100,000 propagating modes. In some embodiments, a smaller diameter multimode fiber, which may propagate fewer modes allowing for a larger bending angle before total speckle decorrelation, could also be used. In some embodiments, multimode fiber endoscope may create a focus in 37 ms at the output plane of the fiber leading to enhancements between 50 and 100 during fiber perturbation. As a result of the known relationship between number of modes and focus enhancement, faster operation could be achieved at the expense of enhancement factor. In some embodiments, a controller implementation may enable the system to perform at a constant rate of, for example, 13 Hz with a 50% duty cycle. In some embodiments, a controller implementation may be configurable and/or the phase mask update protocol could be adapted to the imaging modalities could be implemented. In some embodiments, a multimode fiber system (e.g., a multimode fiber endoscope) can have applications in photodynamic therapy where localized energy delivery may be needed. In some embodiments, a multimode fiber system may be modified for use with dynamic scattering materials such as, for example, biological tissue, neuron imaging, and optogenetics, which may possess decorrelation times on the order of ~10 ms.

Figure 15:
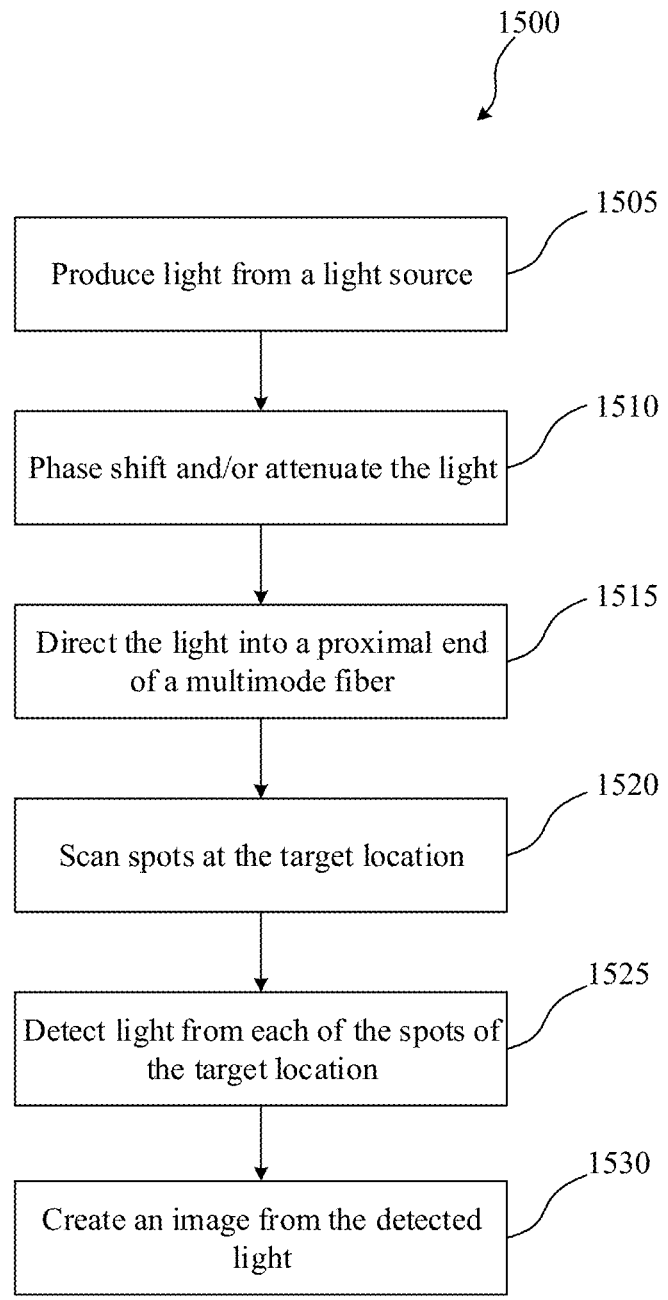
FIG. 15 is a flowchart of an example process for scanning a target area according to some embodiments.

FIG. 15 is a flowchart of an example process 1500 for scanning a target area according to some embodiments. Process 1500 begins at block 1505 where light from a light sources (e.g., light source 105) is produced.

At block 1510 the light may be phase shifted and/or attenuated the light into a first plurality of spatially independent modes. In some embodiments, the light may be phase shifted and/or attenuated using a spatial light modulator (e.g., spatial light modulator 112). In some embodiments, the light may be phase shifted and/or attenuated based on a transmission matrix of the multimode fiber that is created, for example, during a calibration process. The calibration process, for example, may include any calibration process described in this document or any others.

At block 1515 the light may be directed into a proximal end of a multimode fiber to produce a spot at a target location. The multimode fiber may include any multimode fiber or have characteristics of a multimode fiber (e.g., multimode fiber 125) disclosed in this document or any other multimode fiber. The multimode fiber may, for example, produce light with an intensity contrast that is calculated using $$C = \sqrt{\frac{\langle I^2 \rangle}{\langle I \rangle^2} - 1} = \frac{\sigma_I}{\bar{I}}.$$

At block 1520 each of a plurality of spots at the target location may be scanned. The scanning may occur, for example, by moving the target location and/or by moving the endoscope. For example, the each spot of the target location may be illuminated with light from the multimode fiber.

At block 1520 light form each of the plurality of spots of the target location can be detected with a light detector (e.g., detector 135) through the multimode fiber. For example, each spot of the target location can be detected prior to moving to another spot.

At block 1525, an image of at least a portion of the target location can be created from the light detected at each of the plurality of spots. By scanning the multimode fiber from point to point or spot to spot, a portion or all of the target location may be imaged.

The various flowcharts, processes, computers, servers, etc. described in this document may be executed, for example, using the computational system 1600 (or processing unit) illustrated in FIG. 16. For example, the computational system 1600 can be used alone or in conjunction with other components. As another example, the computational system 1600 can be used to perform any calculation, solve any equation, perform any identification, and/or make any determination described here.

The computational system 1600 may include any or all of the hardware elements shown in the figure and described herein. The computational system 1600 may include hardware elements that can be electrically coupled via a bus 1605 (or may otherwise be in communication, as appropriate). The hardware elements can include one or more processors 1610, including, without limitation, one or more general-purpose processors and/or one or more special-purpose processors (such as digital signal processing chips, graphics acceleration chips, and/or the like); one or more input devices 1615, which can include, without limitation, a mouse, a keyboard, and/or the like; and one or more output devices 1620, which can include, without limitation, a display device, a printer, and/or the like.

The computational system 1600 may further include (and/or be in communication with) one or more storage devices 1625, which can include, without limitation, local and/or network-accessible storage and/or can include, without limitation, a disk drive, a drive array, an optical storage device, a solid-state storage device, such as random access memory ("RAM") and/or read-only memory ("ROM"), which can be programmable, flash-updateable, and/or the like. The computational system 1600 might also include a communications subsystem 1630, which can include, without limitation, a modem, a network card (wireless or wired), an infrared communication device, a wireless communication device, and/or chipset (such as a Bluetooth® device, a 802.6 device, a WiFi device, a WiMAX device, cellular communication facilities, etc.), and/or the like. The communications subsystem 1630 may permit data to be exchanged with a network (such as the network described below, to name one example) and/or any other devices described herein. In many embodiments, the computational system 1600 will further include a working memory 1635, which can include a RAM or ROM device, as described above.

The computational system 1600 also can include software elements, shown as being currently located within the working memory 1635, including an operating system 1640 and/or other code, such as one or more application programs 1645, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 1625 described above.

In some cases, the storage medium might be incorporated within the computational system 1600 or in communication with the computational system 1600. In other embodiments, the storage medium might be separate from the computational system 1600 (e.g., a removable medium, such as a compact disc, etc.), and/or provided in an installation package, such that the storage medium can be used to program a general-purpose computer with the instructions/code stored thereon. These instructions might take the form of executable code, which is executable by the computational system 1600 and/or might take the form of source and/or installable code, which, upon compilation and/or installation on the computational system 1600 (e.g., using any of a variety of generally available compilers, installation programs, compression/decompression utilities, etc.), then takes the form of executable code.

The term "substantially" means within 5% or 10% of the value referred to or within manufacturing tolerances.

Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

That which is claimed:

1. An endoscope comprising:
a multimode fiber having a proximal end and a distal end;
a light source disposed relative to the proximal end of the multimode fiber;
a spatial light modulator that phase shifts and/or attenuates the light from the light source into a first plurality of spatially independent modes prior to the light from the light source being directed through the multimode fiber;
a light detector disposed relative to the proximal end of the multimode fiber; and
a plurality of optical elements disposed between the light source and the multimode fiber, wherein one or more of the plurality of optical elements are configured to direct light from the light source into the multimode fiber, and wherein one or more of the plurality of optical elements are configured to direct light from the multimode fiber to the detector.

2. The endoscope of claim 1, wherein the spatial light modulator modulates the light to include a plurality of modes that are substantially decoupled when transmitted through the multimode fiber.

3. The endoscope of claim 1, wherein the multimode fiber includes a plurality of modes, wherein an average difference of eigenvalues of the plurality of modes is maximized.

4. The endoscope of claim 1, wherein the multimode fiber comprises a single multimode fiber.

5. The endoscope of claim 1, wherein the multimode fiber is optimized for robustness to bending while maintaining a well-defined focus.

6. The endoscope of claim 1, wherein the multimode fiber has an intensity contrast greater than 0.7.

7. The endoscope of claim 1, wherein the multimode fiber has an intensity contrast C calculated according to $C=\sigma_I/\bar{I}$, wherein $\sigma_I$ is a variance of intensity ensemble I calculated according to $\sigma_I=\sqrt{<I^2>-<I>^2}$, $\bar{I}$ is average value of the intensity ensemble I, and $<\ldots>$ indicates an ensemble average.

8. The endoscope of claim 1, wherein the multimode fiber is configured to generate speckle patterns at the distal end of the multimode fiber while controlling light wavefronts at the proximal end of the multimode fiber.

9. The endoscope of claim 1, wherein the multimode fiber comprises a graded index multimode fiber.

10. The endoscope of claim 1, wherein the multimode fiber generates a focus with an averaged peak-to-background ratio (n) greater than 500.

11. A system comprising:
a light source;
a spatial light modulator that phase shifts light from the light source into a first plurality of spatially independent modes;
a beam splitter that splits light from the spatial light modulator into a first light beam and a second light beam;
a first imager that images the first light beam;
a multimode fiber coupler that couples a multimode fiber with the system;
a second imager that images light from a distal end of the multimode fiber when coupled with the multimode fiber coupler for each of a second plurality of spatially independent modes; and
a processor coupled with the spatial light modulator, the first imager and the second imager that creates a transmission matrix from the light received at the first imager and the second imager.

12. The system according to claim 11, wherein the first plurality of spatially independent modes is less than the second plurality of spatially independent modes.

13. The system according to claim 11, wherein the first plurality of spatially independent modes comprise a plurality of Hadamard elements of a Hadamard orthonormal basis set.

14. The system according to claim 11, wherein the spatial light modulator comprises a digital micro mirror device.

15. A method for generating an image, the method comprising:
producing light from a light source;
phase shifting and/or attenuating the light into a first plurality of spatially independent modes;
after phase shifting and/or attenuating the light into the first plurality of spatially independent modes, directing the light into a proximal end of a multimode fiber to produce a spot at a target location;
detecting light from the spot of the target location with a light detector through the multimode fiber; and
creating an image of at least a portion of the target location from the light detected at the spot.

16. The method according to claim 15, further comprising:
scanning a plurality of spots at the target location, the plurality of spots including the spot; and
detecting light from each of the plurality of spots at the target location with a light detector through the multimode fiber.

17. The method according to claim 15, wherein the light detected from the target is produced by fluorescent emission, second harmonic generation, and/or a nonlinear process light emission process.

18. The method according to claim 15, wherein phase shifting and/or attenuating the light is based on a transmission matrix of the multimode fiber.

19. The method according to claim 15, wherein phase shifting and/or attenuating the light produces light through the multimode fiber with an intensity contrast greater than 0.7.

20. The method according to claim 15, wherein phase shifting and/or attenuating the light produces light with a plurality of modes, wherein an average difference of eigenvalues of the plurality of modes is maximized.

* * * * *